(12) United States Patent
Faverjon et al.

(10) Patent No.: US 10,442,049 B2
(45) Date of Patent: Oct. 15, 2019

(54) SYSTEM FOR DETECTING A PARTIAL OR TOTAL OBSTRUCTION OF AT LEAST ONE INTERNAL PIPE OF A TOOL

(71) Applicant: SOCIETE DE CONSTRUCTION D'EQUIPEMENT DE MECANISATIONS ET DE MACHINES SCEMM, Saiont-Etienne (FR)

(72) Inventors: Pierre Faverjon, Jonzieux (FR); Cyrille Urville, Saint-Cyprien (FR)

(73) Assignee: SOCIETE DE CONSTRUCTION D'EQUIPMENT DE MECANISATIONS ET DE MACHINES SCEMM, Saint-Etienne (FR)

( * ) Notice: Subject to any disclaimer, the term of this patent is extended or adjusted under 35 U.S.C. 154(b) by 48 days.

(21) Appl. No.: 15/540,621

(22) PCT Filed: Jan. 4, 2016

(86) PCT No.: PCT/EP2016/050026
§ 371 (c)(1),
(2) Date: Jun. 29, 2017

(87) PCT Pub. No.: WO2016/110465
PCT Pub. Date: Jul. 14, 2016

(65) Prior Publication Data
US 2018/0015583 A1    Jan. 18, 2018

(30) Foreign Application Priority Data

Jan. 5, 2015   (FR) ..................... 15 50022

(51) Int. Cl.
*G01M 3/28*    (2006.01)
*B23Q 11/10*   (2006.01)
(Continued)

(52) U.S. Cl.
CPC .......... *B23Q 11/1053* (2013.01); *B23Q 11/10* (2013.01); *B23Q 11/1023* (2013.01);
(Continued)

(58) Field of Classification Search
CPC  B23Q 11/1053; B23Q 11/10; B23Q 17/0904; B23Q 11/1023; B23Q 11/1084;
(Continued)

(56) References Cited

U.S. PATENT DOCUMENTS 3,967,495 A * 7/1976 Wesner ................. G01M 13/02
                                                          73/115.02
5,503,036 A    4/1996 Nguyen et al.
(Continued)

FOREIGN PATENT DOCUMENTS

CN      103446650        * 12/2013
DE    102006052602 A1      4/2008
(Continued)

OTHER PUBLICATIONS

International Search Report corresponding to PCT/EP2016/050026, dated Apr. 8, 2016.
(Continued)

*Primary Examiner* — Robert R Raevis
(74) *Attorney, Agent, or Firm* — Sandberg Phoenix & von Gontard, P.C.

(57) ABSTRACT

The invention primarily relates to a system (10) for detecting a total or partial obstruction of at least one internal fluid pipe (11) of a tool (12), characterized in that said system (10) comprises: a pneumatic system (13) that is intended to be connected upstream of said internal pipe (11) of said tool (12), a pressure source (16) that is connected to said pneumatic system (13) by means of a solenoid valve (17), and a control unit (22) that is configured to open said solenoid valve (17) so as to pressurize said pneumatic system (13),
(Continued)

and then to close said solenoid valve (17) so as to let said pneumatic system (13) be emptied freely by means of said internal pipe (11), and to detect an obstruction state of said internal pipe (11) depending on an analysis over time of a change in the pressure in said pneumatic system (13).

8 Claims, 3 Drawing Sheets

(51) Int. Cl.
    *B23Q 17/09*     (2006.01)
    *G01F 1/74*     (2006.01)
    *G01M 1/36*     (2006.01)
    *G01N 35/10*     (2006.01)
    *G08B 21/18*     (2006.01)

(52) U.S. Cl.
    CPC ...... *B23Q 11/1084* (2013.01); *B23Q 17/0904* (2013.01); *B23Q 17/0909* (2013.01); *B23Q 17/0985* (2013.01); *G01F 1/74* (2013.01); *G01M 1/365* (2013.01); *G01N 35/1016* (2013.01); *G08B 21/182* (2013.01)

(58) Field of Classification Search
    CPC ... B23Q 17/0909; B23Q 17/0985; G01F 1/74; G01M 3/00; G01M 3/02; G01M 1/365; G01M 3/2815; G01N 35/1016; G08B 21/182
    USPC .................................. 73/37, 39, 49.5–49.8
    See application file for complete search history.

(56) References Cited

U.S. PATENT DOCUMENTS

| | | | |
|---|---|---|---|
| 6,647,984 B1 * | 11/2003 | O'Dea | A61M 16/044 |
| | | | 128/207.15 |
| 2007/0169543 A1 | 7/2007 | Fazekas | |
| 2010/0256476 A1 * | 10/2010 | Wood | A61M 16/04 |
| | | | 600/409 |
| 2017/0151403 A1 * | 6/2017 | Higashiyama | A61M 16/04 |

FOREIGN PATENT DOCUMENTS

| | | |
|---|---|---|
| DE | 102007016326 A1 | 10/2008 |
| EP | 1035457 A1 | 9/2000 |
| EP | 2320199 A1 | 5/2011 |
| FR | 2581819 A1 | 11/1986 |
| FR | 2972952 A1 | 9/2012 |
| FR | 2995099 A1 | 3/2014 |
| WO | 9739832 A1 | 10/1997 |

OTHER PUBLICATIONS

Written Opinion corresponding to PCT/EP2016/050026, dated Apr. 8, 2016.

* cited by examiner

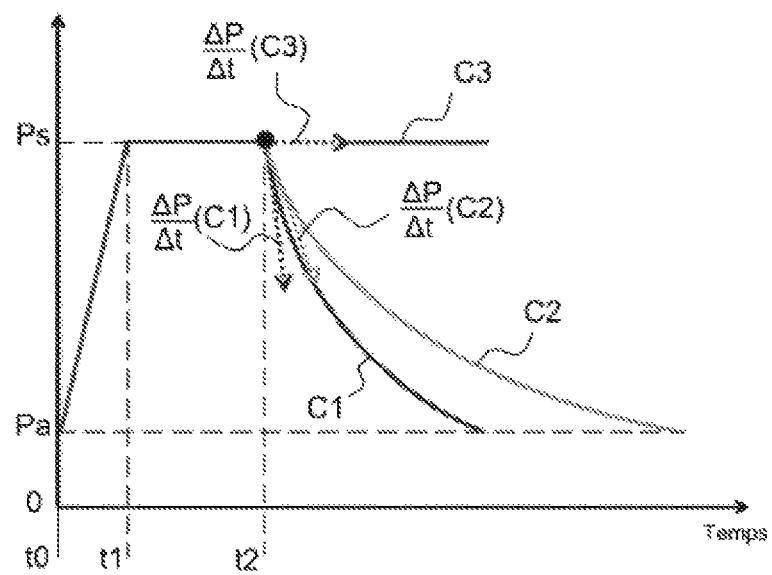

SYSTEM FOR DETECTING A PARTIAL OR TOTAL OBSTRUCTION OF AT LEAST ONE INTERNAL PIPE OF A TOOL

CROSS-REFERENCE TO RELATED APPLICATIONS

This application is the US National Stage application under 35 U.S.C. § 371 of International App. No. PCT/EP2016/050026 filed Jan. 4, 2016 which claims the priority of French application 1550022, filed on Jan. 5, 2015, the contents of which (text, drawings and claims) are incorporated herein by reference.

BACKGROUND

The present invention relates to a system for detecting a total or partial obstruction of at least one internal fluid pipe of a tool. The invention is particularly advantageously, but not exclusively, applicable to the control of machining tools having one or several internal pipes used to supply the functional elements of the tool with liquid or gaseous lubricant or coolant, such as oil, an oil emulsion, a mist made up of air and oil, or the like.

EP 2320199 teaches the implementation of a method for detecting agglomerates of particles in a conduit using a flowmeter. The system determines abrupt changes in flow and provides an alarm signal when the flow rate departs from the expected boundaries. Similarly, document FR 2851819 describes the use of an electrostatic flowmeter measuring the quantity of aggregate particles of a two-phase flow. The detection elements are arranged in a tubular detection element.

However, in the case of tools provided with internal pipes having a small section, such systems are capable of detecting the complete obstruction of the pipes, but not a partial obstruction, since the leak is too small and is not detected. This is due to the limited measuring precision of a standard flowmeter. There is therefore a risk of not detecting a partial obstruction of the internal pipes with a small section, which may deteriorate the operation of the tool, and therefore the manufacturing chain performance.

Furthermore, DE102006052602, DE102007016326 and FR2972982 describe methods making it possible to detect the obstruction of an internal pipe of a tool by comparing a measured pressure to reference pressure curves. However, these methods are based on pressure measurements done in specific configurations that do not make it possible to obtain sufficient measuring accuracy to detect a partial obstruction of pipes having a small section.

SUMMARY

The invention aims to effectively resolve these drawbacks by proposing a system for detecting a total or partial obstruction of at least one internal fluid pipe of a tool. To that end, a system is disclosed which comprises:
a pneumatic system that is intended to be connected upstream from said internal pipe of said tool,
a pressure source that is connected to said pneumatic system by means of a solenoid valve, and
a control unit that is configured to open said solenoid valve so as to pressurize said pneumatic system,
then to close said solenoid valve so as to let said pneumatic system be emptied freely by means of said internal pipe, and to detect an obstruction state of said internal pipe depending on an analysis over time of a change of the pressure in said pneumatic system following the closing of said solenoid valve.

Thus, through the analysis of the change over time of the pressure in the pneumatic system, which is proportional to the pressure loss (blockage) to be detected, the invention makes it possible to guarantee the compliance of internal pipes having a small section of a tool. This is particularly important for micro-lubrication or oil micro pulverizing or MQL (Minimum Quantity Lubrication) tools, for which the absence of obstruction of the pipes conveying the lubricant is a condition for effective operation of the corresponding device.

According to one embodiment, the analysis over time of the change of the pressure comprises measuring a length of time taken by the pneumatic system to return to the ambient pressure after closing of said solenoid valve.

According to one embodiment, the analysis over time of the change in pressure comprises measuring a pressure difference between the pressure at the time of closing said solenoid valve and the pressure at the end of a length of time beginning from the closing of said solenoid valve.

According to one embodiment, the analysis over time of the change of the pressure comprises measuring a duration necessary for said pneumatic system to reach a fixed target pressure after closing of said solenoid valve.

According to one embodiment, said fixed target pressure is greater than the ambient pressure and less than the pressure of said pressure source.

According to one embodiment, the analysis over time of the change of the pressure comprises determining a drift slope of a pressure change curve in said pneumatic system as a function of time following closing of said solenoid valve.

According to one embodiment, said system further includes an electronic chip reader for automatic identification of said tool whose internal pipe must be controlled.

DESCRIPTION OF THE FIGURES

The invention will be better understood upon reading the following description and examining the accompanying figures. These figures are provided purely as an illustration, and are not limiting with respect to the invention.

FIGS. 2a to 2d illustrate different types of analysis over time of the change of pressure in the pneumatic system that may be implemented by the system for detecting the partial or total obstruction of the internal pipe of a tool according to the present invention.

Identical, similar or analogous elements retain the same reference from one figure to the next.

DETAILED DESCRIPTION

Figure 1:
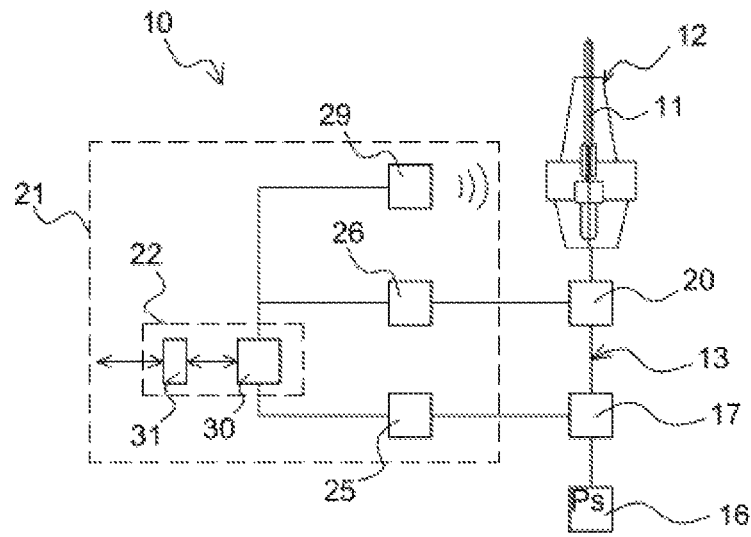
FIG. 1 is a schematic illustration of a system for detecting the partial or total obstruction of an internal pipe of a tool according to the present invention.

FIG. 1 shows a system 10 for detecting a total or partial obstruction of at least one internal fluid pipe 11 of a tool 12, such as a machining tool. The internal pipe(s) 11 to be controlled may for example be used to supply functional elements of the tool with lubricant, such as oil, an oil emulsion, or a mist made up of air and oil. The system 10 may also be used to control cryogenic machining tools 12 comprising at least one internal pipe 11 in which a coolant circulates, for example a nitrogen-based coolant.

The system 10 is preferably used outside of machining operations done by the tool 12, i.e., the tool 12 is first disassembled from the device to which it belongs in order to be mounted on the system 10 for controlling the internal pipe(s) 11. In other words, the system 10 belongs to a station connected to the production. However, alternatively, the system 10 could be integrated into the machining apparatus comprising the tool 12.

To that end, the system 10 includes a pneumatic system 13 connected upstream from the internal pipe 11 of the tool 12. A pressure source 16 is connected to the pneumatic system 13 via a solenoid valve 17. A pressure detector 20 makes it possible to provide the value of the fluid pressure prevailing inside the pneumatic system 13.

Furthermore, the system 10 comprises an electrical control part 21 having a control unit 22 in communication with a control interface 25 suitable for controlling the solenoid valve 17, as well as a module 26 receiving data from the pressure detector 20. The electrical part 21 may also include an electronic chip reader 29, for example of the RFID (Radio Frequency Identification) type for automatic identification of the tool 12 whose pipe 11 must be controlled. The control unit 22 includes means, such as a microcontroller 30, to process and analyze the collected pressure data, as well as a man-machine interface 31 for example made up of a monitor and keyboard or a touch-sensitive screen to allow the operator to interact with the system 10.

Figure 2A:
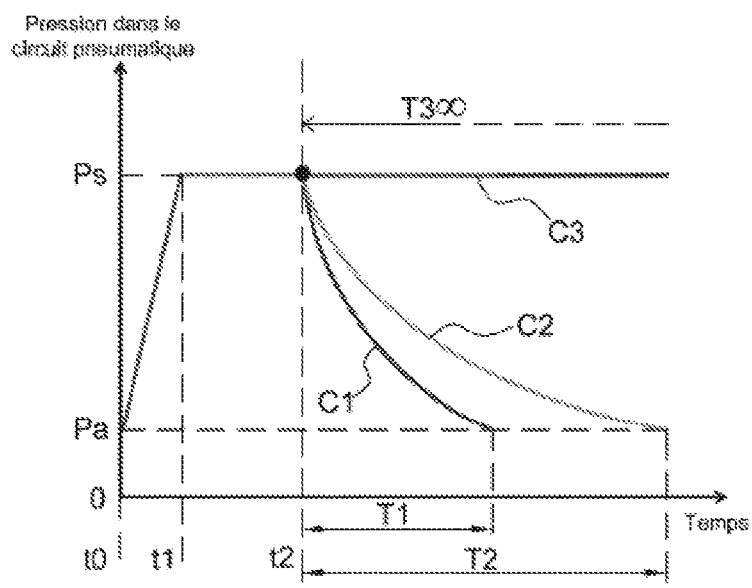

Below, we will provide a more precise description, in reference to FIG. 2a, of the operation of the system 10 for detecting the total or partial obstruction of the pipe 11 of the tool 12.

Between time t0 and t1, the control unit 22 controls, via the interface 25, the opening of the solenoid valve 17 so as to pressurize the pneumatic system 13. Between time t1 and t2, the pressure in the system 13 stabilizes at a pressure substantially equal to the pressure Ps of the source 16.

Beginning at time t2, the control unit 22 controls, via the interface 25, the closing of the solenoid valve 17 so as to allow the system 13 to empty itself freely via the pipe 11.

The control unit 22 then detects the obstruction state of the pipe 11 based on the time taken by the system 13 to return to the ambient pressure Pa after closing of the solenoid valve 17.

Thus, the return to ambient pressure Pa of the pneumatic system 13 is fast (cf. duration T1) in the case of an unobstructed pipe 11, as illustrated by curve C1. The return to ambient pressure Pa is longer (cf. duration T2) in the case of a partially obstructed pipe 11, since the pressure loss slows the flow, as illustrated by curve C2. The system 13 remains pressurized in the case of a completely obstructed pipe 11 due to the absence of flow, as illustrated by curve C3. The duration T3 is therefore infinite due to the absence of flow. In this case, the control unit 22 detects the total obstruction of the internal pipe 11 when it is detected that the ambient pressure Pa has not been reached after a reference duration able to be calibrated based on the application, and in particular the dimensions of the pipe 11.

Figure 2B:
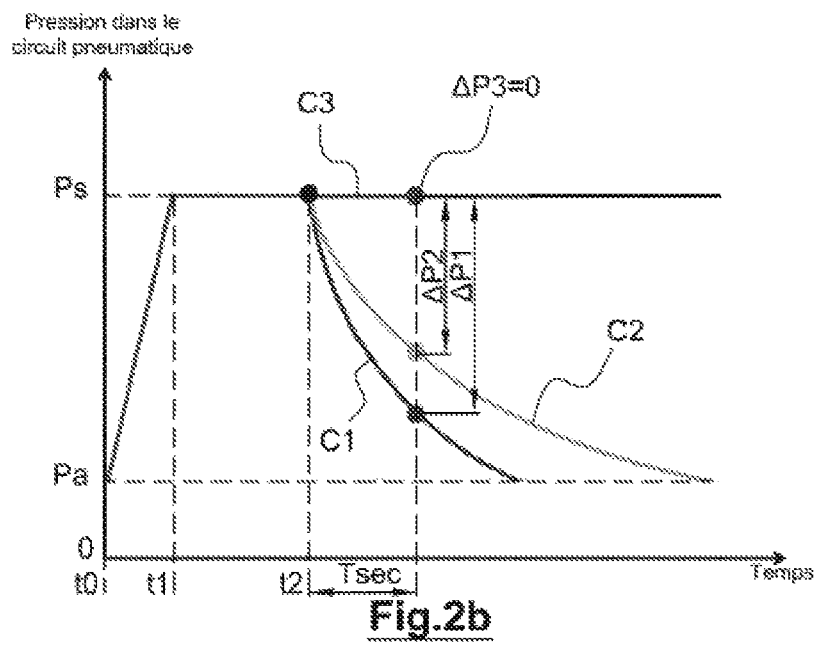

In the alternative embodiment of FIG. 2b, after stabilization of the pressure in the pneumatic system 13, the control unit 22 measures a pressure difference $\Delta P$ between the pressure at the time of closing of the solenoid valve 17 and the pressure after a duration Tsec, for example several seconds, beginning from closing of the solenoid valve 17. Thus, one observes that this pressure difference is significant (cf. difference $\Delta P1$) in the case of an unobstructed pipe 11, as illustrated by curve C1. This pressure difference is smaller (cf. difference $\Delta P2$) in the case of a partially obstructed pipe 11, since the pressure loss slows the flow, as illustrated by curve C2. In the case of a completely obstructed pipe 11, the pressure difference is zero (cf. difference $\Delta P3$) due to the absence of flow, as illustrated by curve C3.

Figure 2C:
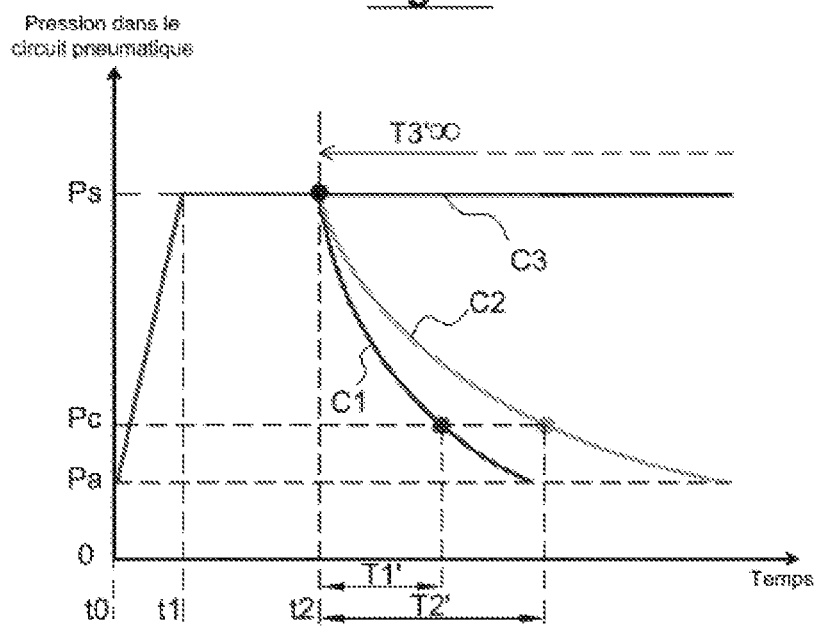

In the alternative embodiment of FIG. 2c, after the stabilization of the pressure in the pneumatic system 13, the control unit 22 measures the duration necessary for the pneumatic system 13 to reach a fixed target pressure Pc after closing of the solenoid valve 17. This target pressure Pc is greater than the pressure Pa and less than the pressure Ps of the pressure source 16. The advantage of this embodiment is that it is faster to implement than the embodiment of FIG. 2a.

Thus, one can see that the duration to reach the target pressure Pc is short (cf. duration T1') in the case of an unobstructed pipe 11, as illustrated by curve C1. This duration is greater (cf. duration T2') in the case of a partially obstructed pipe 11, since the pressure loss slows the flow, as illustrated by curve C2. It will be noted that the durations T1' and T2' are respectively shorter than the durations T1 and T2 obtained for identical curves C1 and C2. In the case of a completely obstructed pipe 11, the duration will be infinite (cf. duration T3') due to the absence of flow, as illustrated by curve C3. In this case, the control unit 22 detects the total obstruction of the internal pipe 11 when it is detected that the target pressure Pc has not been reached after a reference duration able to be calibrated based on the application, and in particular dimensions of the pipe 11.

In the alternative embodiment of FIG. 2d, after the stabilization of the pressure in the pneumatic system 13, the control unit 22 determines the drift slope $\Delta P/dt(Ci)$ of the pressure change curve Ci in the pneumatic system 13 as a function of time after closing of the solenoid valve 17. Thus, one can see that the slope is steep (cf. slope $\Delta P/dt(C1)$) in the case of an unobstructed pipe 11, as illustrated by curve C1. The slope is gentler (cf. slope $\Delta P/dt(C2)$) in the case of a partially obstructed pipe 11, since the pressure loss slows the flow, as illustrated by curve C2. In the case of a completely obstructed pipe 11, the slope is zero (cf. slope $\Delta P/dt(C3)$) due to the absence of flow, as illustrated by curve C3.

In all of the considered cases, the invention is based on the analysis of the change over time of the pressure in the pneumatic system 13, which is proportional to the pressure loss (blockage) to be detected. The invention thus makes it possible to guarantee the compliance of the internal pipes 11 of the tool 12. This is even more important for micro-lubrication or oil micro-pulverizing or MQL (Minimum Quantity Lubrication) tools, for which the absence of obstruction of the pipes 11 conveying the lubricant is a condition for efficient operation of the tool 12.

The invention claimed is:

1. A system for detecting a total or partial obstruction of at least one internal fluid pipe of a tool, wherein said system comprises:
    a pneumatic system adapted to be connected upstream from said at least one internal pipe of said tool,
    a pressure source that is connected to said pneumatic system by means of a solenoid valve, and
    a control unit; said control unit being configured:
        initially to open said solenoid valve so as to pressurize said pneumatic system,
        then, after said pneumatic system has reached a pressure substantially equal to pressure of said pressure source, to close said solenoid valve so as to let said pneumatic system be emptied freely by means of said internal pipe, and to analyze the change in pressure in said pneumatic system over time following the closing of said solenoid valve to determine the presence of an obstruction in said internal fluid pipe of said tool.

2. The system according to claim 1, wherein the analysis over time of the change of the pressure comprises measuring a length of time (T1-T3) taken by the pneumatic system to return to the ambient pressure (Pa) after closing of said solenoid valve.

3. The system according to claim 1, wherein the analysis over time of the change in pressure comprises measuring a pressure difference ($\Delta P1$-$\Delta P3$) between the pressure at the time of closing said solenoid valve and the pressure at the end of a length of time (Tsec) beginning from the closing of said solenoid valve.

4. The system according to claim 1, wherein the analysis over time of the change of the pressure comprises measuring a duration (T1'-T3') necessary for said pneumatic system to reach a fixed target pressure (Pc) after closing of said solenoid valve.

5. The system according to claim 4, wherein the fixed target pressure (Pc) is greater than the ambient pressure (Pa) and less than the pressure (Ps) of said pressure source.

6. The system according to claim 1, wherein the analysis over time of the change of the pressure comprises determining a drift slope ($\Delta P/dt(C1)$-$\Delta P/dt(C3)$) of a pressure change curve (C1-C3) in said pneumatic system as a function of time following closing of said solenoid valve.

7. The system according to claim 1, wherein said system further includes an electronic chip reader for automatic identification of said tool.

8. A method for detecting a total or partial obstruction of an internal fluid pipe of a tool, said method comprising:
   connecting said tool to a pneumatic system to place the internal fluid pipe in communication with the pneumatic system; said pneumatic system being operatively connected to a pressure source by means of a solenoid valve;
   opening said solenoid valve to pressurize said pneumatic system,
   closing said solenoid valve after said pneumatic system has reached a pressure substantially equal to a pressure of said pressure source and allowing said pneumatic system be emptied freely by means of said internal fluid pipe, and
   electronically analyzing the change in pressure in said pneumatic system over time following the closing of said solenoid valve to determine the presence of an obstruction in said internal fluid pipe of said tool.

* * * * *